US006923409B2

(12) United States Patent
Strunk

(10) Patent No.: US 6,923,409 B2
(45) Date of Patent: *Aug. 2, 2005

(54) TOOTH BRUSH HOLDER

(76) Inventor: Peter Strunk, P.O. Box B, Del Mar, CA (US) 92014

( * ) Notice: Subject to any disclaimer, the term of this patent is extended or adjusted under 35 U.S.C. 154(b) by 136 days.

This patent is subject to a terminal disclaimer.

(21) Appl. No.: 10/102,362

(22) Filed: Mar. 19, 2002

(65) Prior Publication Data

US 2002/0096607 A1 Jul. 25, 2002

Related U.S. Application Data

(63) Continuation-in-part of application No. PCT/US01/02592, filed on Jan. 26, 2001, and a continuation-in-part of application No. 09/494,094, filed on Jan. 28, 2000, now Pat. No. 6,371,420.

(51) Int. Cl.$^7$ .............................................. A46B 17/02
(52) U.S. Cl. .................... 248/111; 248/315; 15/105; 368/10
(58) Field of Search ................................ 248/110, 111, 248/112, 113, 314; 368/10, 107; 15/167.1, 167.2, 236.88

(56) References Cited

U.S. PATENT DOCUMENTS

| 2,501,822 A | 3/1950 | Kuyler |
| 2,926,487 A | 3/1960 | Stone |
| 3,998,234 A | 12/1976 | Stubbmann |
| 4,285,151 A | 8/1981 | Gertler |
| 5,044,037 A | 9/1991 | Brown |
| 5,184,959 A | 2/1993 | Oryhon |
| 5,570,325 A | 10/1996 | Arpadi |
| 5,676,279 A | 10/1997 | Bastion |
| 5,864,288 A | 1/1999 | Hogan |
| 5,875,796 A | 3/1999 | Silver-Isenstadt |
| 5,894,453 A | 4/1999 | Pond |
| 5,960,507 A | 10/1999 | Dutra |
| 6,074,076 A | 6/2000 | Parrish-Bhagwat |

FOREIGN PATENT DOCUMENTS

| EP | 0032869 | 1/1980 |
| GB | 2324174 A | 11/1998 |
| JP | 11318951 | 11/1999 |

Primary Examiner—Gwendolyn Baxter
(74) Attorney, Agent, or Firm—Roberts & Roberts, LLP

(57) ABSTRACT

A tooth brush holder having a base plate, a rotating cover, and a receptacle therein for receiving a tooth brush. The cover has at least one opening in alignment with the receptacle. The base plate includes facilities for closing the receptacle when the tooth brush is removed so that the user cannot replace the tooth brush until a predetermined time has elapsed.

41 Claims, 2 Drawing Sheets

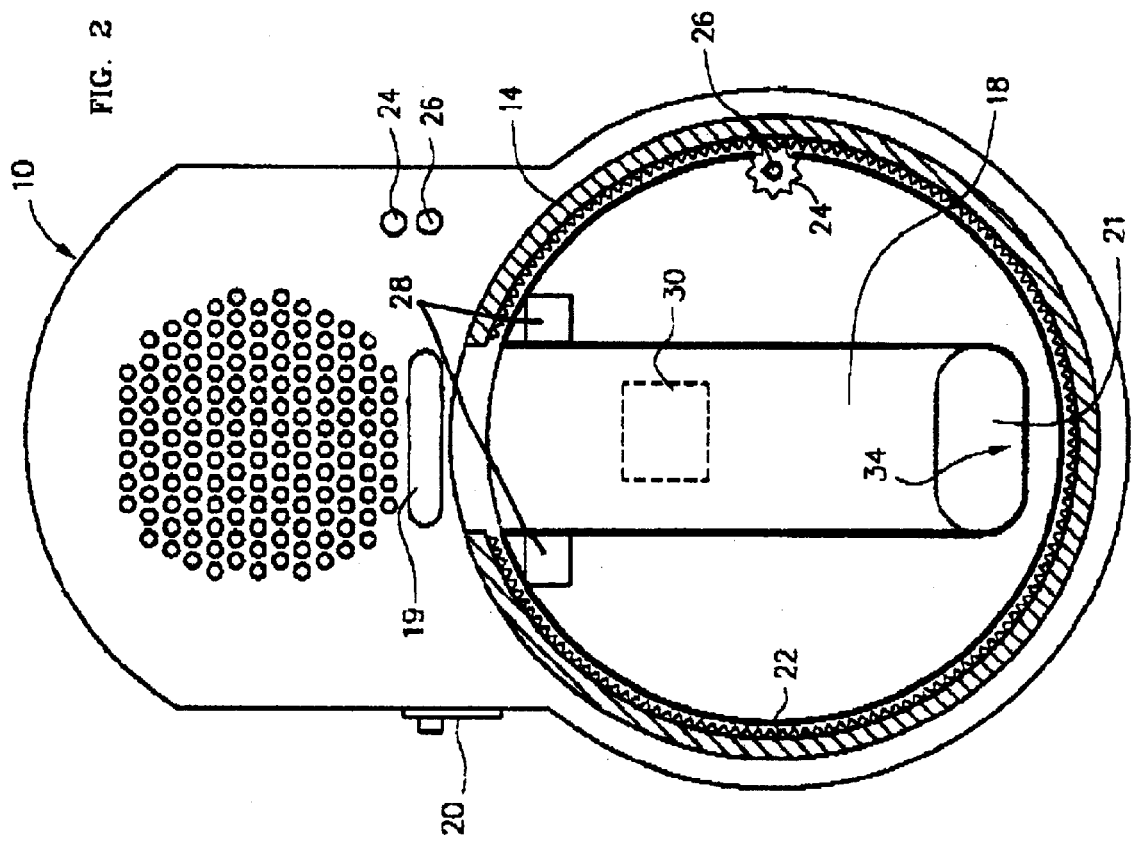
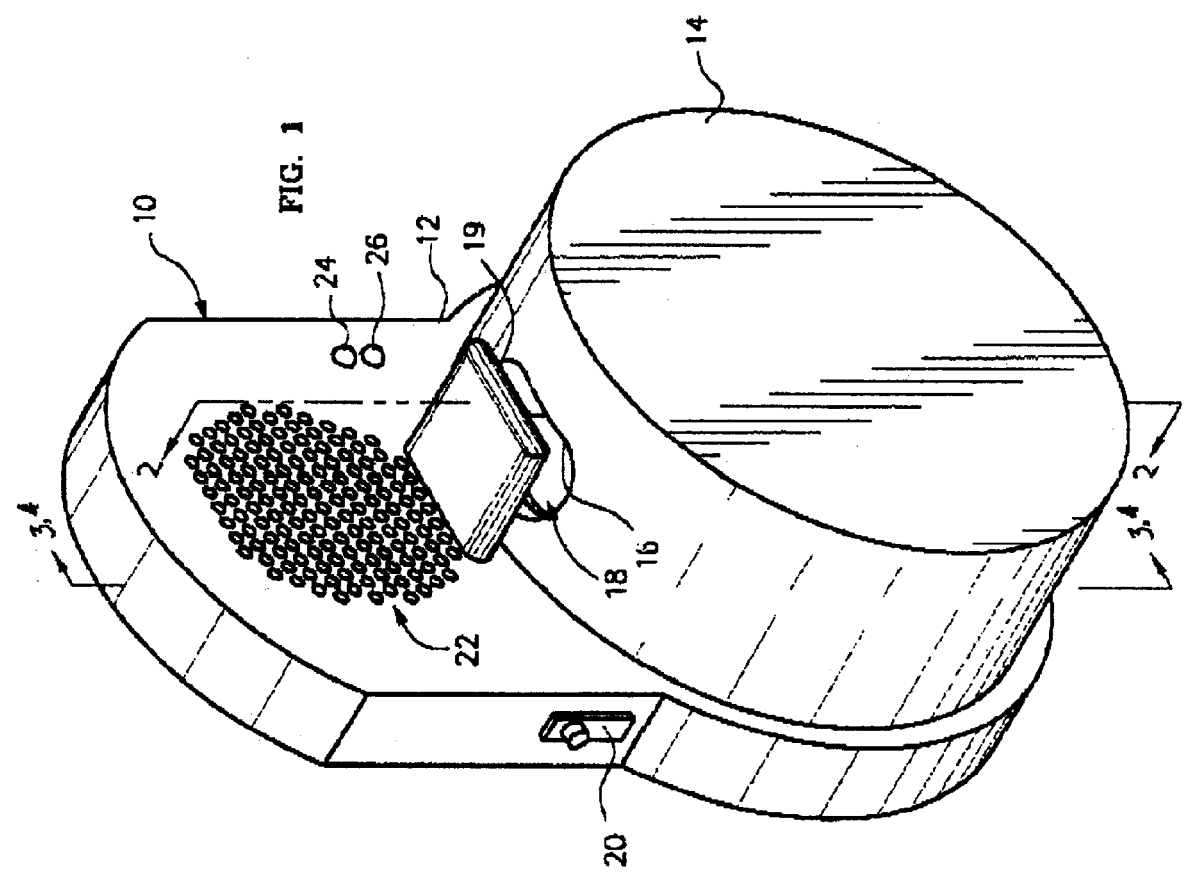

TOOTH BRUSH HOLDER

PRIORITY CLAIM

This application is a continuation-in-part application of U.S. application Ser. No. 09/494,094, filed Jan. 28, 2000 now U.S. Pat. No. 6,371,420 and is a continuation-in-part of PCT Application No. PCT/US01/02592 filed Jan. 26, 2001 and claims priority from both previously filed applications.

BACKGROUND OF THE INVENTION

1. Field of the Invention

This invention relates generally to an improved tooth brush holder, and specifically to a tooth brush holder and timer for encouraging the brushing of teeth for a predetermined period of time. The tooth brush holder and timer includes a receptacle for receiving the handle of the tooth brush, means for closing the receptacle when the tooth brush is removed and for keeping the receptacle closed for a predetermined period of time. The subject invention is useful for the improvement of dental health. It is based on three considerations. First, brushing teeth has been proven to be essential to maintain and improve dental health. Second, a substantial portion of the population practices insufficient brushing according to the standard recommended by dental health care professionals. Third, improvements in the tooth brushes and tooth paste are largely ineffective if they are not used for a sufficient time. The subject invention encourages and influences the user to brush longer and more frequently achieving improved results.

2. Description of Related Art

Kuyler U.S. Pat. No. 2,501,822 discloses a tooth brush holder which when a tooth brush is removed allows music to play. The object of the invention is to encourage a child to brush his/her teeth.

Hogan U.S. Pat. No. 5,864,288 discloses a talking tooth brush holder. When a tooth brush is removed from the holder a sound producing device is activated to produce sound for a predetermined period of time. If the tooth brush is prematurely replaced a warning message of light is activated to remind the user to brush further.

Oryhon et al. U.S. Pat. No. 5,184,959 discloses a programmable tooth brush alarm unit which provides either a visual or audible alarm at a pre selected brushing time.

Arpadi U.S. Pat. No. 5,570,325 discloses a timer device for presenting an amusing visual representation of the time required for a child to brush their teeth.

The United Kingdom patent application of Webb GB 2324174 A discloses a timing device that is automatically activated upon removal of a tooth brush. One embodiment of the device includes a stop member that prevents the toothbrush from being replaced until a predetermined amount of time has passed.

Parrish-Bhagwat U.S. Pat. No. 6,074,076 discloses a timer device for presenting an amusing visual representation of the time required for a child to brush their teeth.

Stubbmann U.S. Pat. No. 3,998,234 discloses a timer device that incorporates visual and audio stimulus to encourage a child to brush their teeth. One embodiment of the device includes a timer to indicate the time that the child has brushed their teeth.

None of the prior art discloses the tooth brush holder of the present application.

SUMMARY OF THE INVENTION

This invention relates to a tooth brush holder. The invention is an improvement over the tooth brush holders disclosed in U.S. application Ser. No. 09/494,094, filed Jan. 28, 2000 and PCT Application No. PCT/US01/02592 filed Jan. 26, 2001. The disclosures of both of those applications and their file histories are incorporated herein by reference.

The improved tooth brush holder of the present application has a base plate, a rotatable cover and a receptacle for receiving a tooth brush. In its resting state, an opening in the rotatable cover is aligned with the opening of the receptacle. A tooth brush handle extends through the opening in the cover and into the receptacle. When the tooth brush is removed, the cover begins to rotate. Once the cover begins to rotate, the opening in the cover is no longer aligned with the opening of the receptacle. Thus, the tooth brush may not be placed back into the receptacle until an opening in the cover is once again aligned with the opening of the receptacle. Accordingly, a user is encouraged to continue brushing their teeth until an opening in the cover is once again aligned with the opening of the receptacle and the tooth brush can be replaced. A user thus may be encouraged to brush for an appropriate length of time by designing the tooth brush holder so that an opening in the cover does not align with the opening of the receptacle until an appropriate length of time has passed.

In addition to the above, the tooth brush holder may include an audio program that plays while a user is brushing their teeth. Such an audio program may be supplied and reproduced through any known means including, but not limited to, recording the audio program in a memory means and reproducing the audio program by means of decoding and amplification circuitry connected to a speaker. In the preferred embodiments, all of the tooth brush holder components involved in the production of an audio program are located within the base plate of the tooth brush holder.

The following examples of audio programs are given merely to illustrate a few of the possible programs and are not intended to limit the scope of the invention in any way. Such an audio program may be music of any type. Alternatively, the audio program may consist of one or more spoken materials. In the case of such spoken materials, it is preferred that a variety of spoken materials be produced so that a different piece of spoken material is played each time the tooth brush holder is activated. Examples of such spoken material may include, without limitation, jokes, obscure words and their definitions to expand a user's vocabulary, foreign words and their translation in the user's native language, motivational or self-empowerment materials, or advertising materials promoting goods or services. An additional category of audio programs, offered without limitation, include nature sounds such as the sounds of surf, running water, whale songs, or bird songs. A final example, given without limitation, is that the tooth brush holder may include a radio that is activated when the tooth brush holder is activated. In the case of a radio, the radio may be tunable so that a variety of different radio stations may be received. Alternatively, the radio may be set on a particular station. The latter case may be useful as a promotional item for the particular radio station that is received. An additional alternative is to combine one or more different types of audio programs so that a user may, for example but without limitation, hear a joke upon one activation of the tooth brush holder, a vocabulary word upon the next activation, and a nature sound upon the following activation. If desired, the audio program of a tooth brush holder may be activated independently of whether a the tooth brush holder is activated. Such a feature allows consumers to sample the audio program before purchasing a tooth brush holder or could allow a user to turn the audio program off if the user no longer wishes to listen to the audio program. A volume adjustment feature also may be included if desired.

The preferred shape of the cover of the tooth brush holder is a short cylinder, however, the cover shape may be any shape provided the chosen shape may be rotated to close off the opening of the receptacle. By way of example, but without limitation, the cover may be hemispherical. In addition, various materials may be applied on top of the cover to change the shape, appearance, texture, etc., of the tooth brush holder. Such overlays may be attached to the cover so that the overlay rotates with the cover or such overlays may be independent of the cover such that they do not rotate at all or rotate at a different speed or in the opposite direction from the cover. In addition, the cover material or overlay material may have openings that, when combined with artwork or other features behind such openings, lead to an enhanced visual effect. In addition the tooth brush holder may include one or more light sources that may or may not be synchronized with the audio program or specific points of rotation to achieve desired aesthetic effects. Such light sources may be located at virtually any point on the tooth brush holder such as, without limitation, on the base plate, on the rotating cover, or under the rotating cover. Such light sources may be any known light source. In addition, the cover may be made from transparent or translucent materials to further enhance the visual effect of the tooth brush holder.

Such arrangements provide for a nearly limitless array of possibilities for designs that may appeal to consumers. For example, but without limitation, a picture of the planet earth viewed from space attached to an overlay that does not move with the rotating cover may be combined with a picture of the moon that is attached to the end of a projection from the rotating cover. Thus, when the tooth brush holder is activated and the cover rotates, the picture of the moon rotates around the earth. Such an arrangement may be adapted to a virtually limitless number of consumer appealing designs. A second example, given without limitation, is to provide an overlay that includes some gaps or holes and rotates in the direction opposite to the direction of rotation of the underlying cover and to incorporate a psychedelic design typical of the 1960's or 1970's on both the cover and the overlay so that when the tooth brush holder is activated a type of moving kaleidoscope effect is generated.

The reader will appreciate that the present invention may be adapted to an nearly infinite number of variations and permutations to fit virtually any consumer context or marketing environment. Such adaptation may be accomplished without significant modification of the basic unit. Thus, such adaptations may be accomplished at a minimum of cost. The ability to generate a near infinite variety of tooth brush holders without the need to customize the manufacturing for each variation is considered to be an important feature of the invention.

In the preferred embodiment, most or all of the electronic components of the tooth brush holder are located within the base plate and are relatively isolated from the cover and receptacle. Such an arrangement is advantageous because it reduces the chance of water, tooth paste residue, or other such foreign substances from contacting the electronic components and adversely affecting the functioning of the tooth brush holder.

The improved tooth brush holder has a receptacle therein for receiving the handle of a tooth brush. The receptacle preferably has a drain. In the preferred embodiment, the receptacle and drain are structured to (1) support the tooth brush; (2) allow drainage of any water and residue that may drain from the tooth brush without requiring an opening in the rotating cover to allow such drainage; (3) isolate such water and residue within the receptacle and drain component of the tooth brush holder and away from the mechanical, electronic, and other components of the tooth brush holder; and (4) minimize the chance of any blockage of the drain by accumulated residue or any other foreign matter. It is preferred to structure the receptacle as small as possible to reduce the total bulk of the tooth brush holder, however, the receptacle should also be structured to accommodate as may different shapes of tooth brushes as possible. The preferred footprint of the receptacle is ovular with the long axis of the oval perpendicular to the axis of rotation of the cover. Such an arrangement minimizes the total depth of the tooth brush holder, accepts most shapes of tooth brush, and minimizes the chance that an irregularly-shaped tooth brush, such as a child's tooth brush that incorporates the three dimensional shape of a cartoon character into the handle, will become jammed in the receptacle.

In the preferred embodiment, the cover rotates about a center axle that links the cover to the receptacle which is attached in turn to the base plate. Note, however, that other means may be used to position the cover appropriately and rotatably attach the cover to the base plate. One example, given without limitation, is to incorporate an flange around the interior or exterior circumference of the cover that fits into a corresponding groove of the base plate.

The rotation of the cover may be accomplished by a motor. Preferably, the motor turns at 6,000 revolutions per minute or more. It is recommended, however, that a user brush their teeth for at least two or three minutes. Accordingly, if the rotating cover is provided with one opening, the cover should rotate at a speed not faster than 0.5 revolution per minute. Thus, in the preferred embodiment, the motor is connected to a gear box to reduce the speed of rotation an appropriate amount. Such gearing also increases the force with which the cover turns. One alternative to a relatively high speed motor and additional gearing is to provide the tooth brush holder with a fixed relatively low speed motor or variable speed motor run at a relatively low speed.

In the preferred embodiment, the motor and the gear box are located within the base plate. The drive shaft of the gear box extends through the base plate and into the interior space defined by the rotatable cover. If desired, the opening in the base plate through which the drive shaft of the gear box extends may be sealed with a gasket or other know sealing means to further isolate the electrical components located within the base plate.

In the preferred embodiment, gear teeth are located on the interior surface of the rotatable cover. Such teeth shall be referred to as cover gear teeth. The cover gear teeth may be integrated into the cover during the manufacture of the cover or the cover gear teeth may be provided as a separate component that is attached to the cover through conventional means. In the preferred embodiment, the cover gear teeth are located on the interior annular surface of the cover, immediately adjacent to the surface of the base plate. A drive gear is attached to the drive shaft of the gear box. The teeth of the drive gear mesh with the cover gear teeth so that rotation of the motor causes rotation of the drive gear which in turn causes rotation of the cover. In the case of a relatively low speed motor or a variable speed motor turning at relatively low speed, the drive gear may be connected directly to the motor shaft.

The previous described arrangement of a high speed motor and additional gearing is the preferred arrangement of the driving mechanism of the tooth brush holder. A variety of other driving mechanisms, however, may be used to accomplish the rotation of the cover. For example, but without limitation, the cover gear teeth may be placed on the exterior surface of the cover and the motor, shaft, drive gear, and, if desired, additional gearing may be positioned appropriately to allow activation of the motor to result in rotation of the cover. As a second example, given without limitation, the cover gear teeth may be positioned at any point on the interior annular surface of the cover. As a third example, given without limitation, the cover gear teeth may be positioned on an annular ring that protrudes towards the base plate from the interior surface of the cover that faces the base plate. Such an annular ring may be positioned at virtually any radial distance from the center of rotation of the cover. In addition, the cover gear teeth may be placed on the side of the annular ring that faces the center of rotation of the cover or may be placed on the opposite side of the annular ring. As a fourth example, given without limitation, the outer circumference of the axle itself may be provided with gear teeth. In each of the foregoing examples, the motor, drive shaft, drive gear, and if appropriate, additional gearing should be positioned appropriately to allow activation of the motor to result in rotation of the cover. A final alternate drive mechanism, given without limitation, is to connect the motor directly or indirectly to the center of rotation of the cover.

The cover may be provided with one or more openings that can align with the opening of the receptacle. If the cover has only one opening, the cover must rotate a full 360 degrees before the opening in the cover is realigned with the opening of the receptacle and the tooth brush may be replaced. If the cover is provided with two openings, the openings may be provided directly opposite each other so that an opening is aligned with the opening of the receptacle after the cover rotates 180 degrees. As disclosed in U.S. application Ser. No. 09/494,094, filed Jan. 28, 2000 and PCT Application No. PCT/US01/02592 filed Jan. 26, 2001, such an arrangement may be used to persuade a user to brush twice per day. Similarly, the cover may be provided with three openings to encourage a user to brush three times per day. Alternatively, the cover may be provided with seven openings to encourage a user to brush once each day of the week. The foregoing examples are given without intent to limit the invention to tooth brush holders with covers having the specified number of openings. Covers with any number of openings are considered to be within the scope of the invention.

The amount of time that passes from when the cover begins rotating until an opening in the cover realigns with the opening of the receptacle may be determined by the rotation speed of the cover. The rotation speed of the cover may be varied in a number of ways. For example, but without limitation, the rotation speed of the cover may be set at the time of manufacture of the tooth brush holder by manufacturing the tooth brush holder with a motor that runs at a constant speed and, if desired, incorporating gearing between the motor and the drive gear of the cover that results in the cover being rotated at a predetermined speed. Alternatively, but without limitation, a variable speed motor may be used to drive the rotation of the cover and the speed may be preset. An additional alternative, given without limitation, to adjust the time period between removal of the tooth brush and realignment of a cover opening with the receptacle opening is to pause the rotation of the cover one or more times while the opening in the cover is not aligned with the opening of the receptacle. An additional alternative, offered without limitation, is to begin by rotating the cover in one direction for a predetermined period of time and then rotate the cover in the opposite direction to align an opening in the cover with the opening of the receptacle. In the case of a cover that reverses rotation direction, the cover opening that is aligned with the receptacle opening usually will be the same cover opening that was aligned with the receptacle before the start of rotation, however, the tooth brush holder may be constructed such that a different opening is aligned at the conclusion of the rotation cycle.

In the preferred embodiment, the tooth brush holder is provided with electronic circuitry that controls the operation of the tooth brush holder. Such circuitry shall be referred to as the control mechanism. The control mechanism may perform and control a variety of different functions. For example, but without limitation, the control mechanism may receive signals from a detecting mechanism that indicate the presence or absence of a tooth brush in the receptacle and either stop or start the rotation of the cover in response to such signals. For example, but without limitation, the control mechanism may receive a signal from the detecting mechanism indicating that a tooth brush has been removed from the receptacle. Accordingly, the control mechanism may start the rotation of the cover. Alternatively, the control mechanism may receive a signal from the detecting mechanism indicating that an object such as a child's finger has been introduced into an opening of the cover and the opening of the receptacle. Accordingly, the control mechanism may stop the rotation of the cover. The control mechanism also may control the speed of cover rotation if a variable speed motor is used. If the rotation of the cover is paused or reversed or both, the control mechanism may control those actions. The control mechanism may keep track of whether or not a cover opening is aligned with the opening of the receptacle and may stop, start, reverse, or continue the rotation of the cover as is appropriate. If the cover is provided with multiple openings, the control mechanism may keep track of the location of one or more of such openings with respect to the receptacle and may stop, start, reverse, or continue the rotation of the cover as is appropriate. The control mechanism may also start or stop the audio program. The control mechanism may also control any lights or other visual entertainment program. The control mechanism may also keep track of total accumulated run time and may indicate to a user when it is time to replace the user's tooth brush. Such an indication may, for example but without limitation, be the illumination of a particular light, an announcement through the audio program, or both. Preferably, the improved tooth brush holder is provided with means to set the total accumulated time to zero to correspond to the replacement of a tooth brush.

As stated above, the tooth brush holder has a detecting mechanism that detects the presence or absence of a tooth brush or other object within the receptacle and generates a corresponding signal. The detecting mechanism may consist of a mechanical switch. Such a switch may be located within the receptacle or proximate to the opening of the receptacle. An example of a mechanical switch that is located within the receptacle is shown in U.S. application Ser. No. 09/494,094, filed Jan. 28, 2000 and in PCT Application No. PCT/US01/02592 filed Jan. 26, 2001.

A preferred form of mechanical switch consists of a protruding element that blocks the opening of the cover and receptacle so that a tooth brush may not be inserted into the receptacle without moving the protruding element. For example, but without limitation, the protruding element may be biased to protrude perpendicularly outward from the base plate. When a user wishes to insert a tooth brush into the receptacle, the user pushes against the protruding element and moves the protruding element at least partially back into the base plate. The protruding element may be shaped so that a generally downward force is translated into a generally horizontal force that moves the protruding element at least partially back into the base plate. For example, but without limitation, the edge of the protruding element opposite the cover opening may be rounded or sloped. Sensing means may be used to determine whether the protruding element is fully extended indicating the absence of a tooth brush in the receptacle or whether the protruding element is positioned partially back within the base plate indicating the presence of a tooth brush. One example of such sensing means, provided without limitation, may be a micro switch. Alternatively, sensing means may be included that detect movement of the protruding element, and if desired, the direction of such movement. Such movement will indicate a change of state with respect to the presence or absence of a tooth brush within the receptacle. If the direction of such movement also is detected, that direction will indicate whether the change of state corresponds to an insertion of a tooth brush or the removal of a tooth brush. Preferably, such sensing means are located within the base plate to minimize the possibility of water, tooth paste residue, or other such foreign material adversely affecting the functioning of the improved tooth brush holder. If desired, the protruding element may be further isolated from the electrical components of the tooth brush holder by a gasket, water proof membrane or other known sealing means to further minimize the chance of a malfunction.

A second example of a preferred mechanical switch, offered without limitation, consists of a protruding element that operates as a lever with a pivot point located at or near the surface of the base plate proximate to the opening of the rotating cover and the receptacle. The portion of the protruding element that extends out from the base plate is positioned so that the protruding element is partially rotated about its pivot point when a user inserts a tooth brush into the receptacle. In this case, the protruding element may be biased in a generally upward direction away from the opening of the opening of the rotating cover. Sensing means may be used to determine whether the protruding element is in its biased resting position indicating the absence of a tooth brush in the receptacle or whether the protruding element is partially pivoted indicating the presence of a tooth brush. Alternatively, sensing means may be included that detect pivotal movement of the protruding element, and if desired, the direction of such movement. Such movement will indicate a change of state with respect to the presence or absence of a tooth brush within the receptacle. If the direction of such movement also is detected, that direction will indicate whether the change of state corresponds to an insertion of a tooth brush or the removal of a tooth brush. Preferably, such sensing means are located within the base plate to minimize the possibility of water, tooth paste residue, or other such foreign material adversely affecting the functioning of the improved tooth brush holder. If desired, the protruding element may be further isolated from the electrical components of the tooth brush holder by a gasket, water proof membrane or other known sealing means to further minimize the chance of a malfunction.

In addition to the above, without limitation, any energy-based emitter and receiver such as emitters and receivers based on visible, infra-red, or other light, radar, sonar or any other energy that may be emitted and detected by the components of the detecting mechanism and absorbed, reflected, or deflected by a tooth brush or other object may be used as a detecting mechanism.

An additional alternative detecting mechanism, offered without limitation, may be an electromagnetic sensor. If an electromagnetic sensor is used, such a sensor may detect the presence of metal or other electromagnetically active material within a certain distance of the sensor. Such metal or other material may be either integrated into the handle of a tooth brush during the manufacture of the tooth brush or may be attached to the tooth brush by a variety of different means such as combining the metal or other material with an adhesive or elastic substance that may facilitate the attachment of the metal or other material to the handle of a tooth brush.

Finally, any other means known in the art to detect the presence or absence of a tooth brush or to detect a change in state with respect to the presence or absence of a tooth brush may be used as a detecting mechanism.

The detecting mechanism may be located at any point on the tooth brush holder. For example, but without limitation, the detecting mechanism may be located at or near the top opening of the receptacle. Such a location may be particularly useful in the case of a detecting mechanism that operates by detecting the interruption, deflection, absorption, or reflection of emitted energy because such a detecting mechanism may detect not only the presence of a tooth brush being placed in the receptacle but also a child's finger being stuck in the receptacle thus avoiding closing the receptacle on a child's finger. If the detecting mechanism is based on electromagnetic detection means, the detecting mechanism may, for example but without limitation, be located entirely outside of the receptacle. Such a location may be particularly advantageous because it minimizes the chances of moisture, tooth paste residue, and other foreign substances interfering with the detecting mechanism.

The logic by which the control mechanism detects the removal of a tooth brush from the receptacle may be based on any of a number of different systems. For example, but without limitation, the detecting mechanism may generate a signal indicating that the tooth brush is present, or it may generate a signal indicating that the tooth brush is absent. Such a signal may be constant or the control mechanism may query the detecting mechanism to check for the presence or absence of a tooth brush at regular predetermined time intervals. Alternatively, the logic system may operate by detecting a change in state. The change in state signal may cause the control mechanism to query the detecting mechanism to determine whether a tooth brush is present or absent. Alternatively, the last know state, such as the tooth brush being present, may be stored in a memory component of the control mechanism and, upon detection of a change in state the opposite state, such as the tooth brush being absent, will be assumed by the control mechanism. In addition to the foregoing, any other logic system known in the art may be used to detect the removal of a tooth brush from the receptacle.

Although the use of a control mechanism is preferred, the principles of this invention may be practiced by connecting the power supply to a mechanical switch that also functions as both the detecting mechanism and the control mechanism that starts and stops the motor. In such a case, when the tooth brush is removed from the receptacle, the mechanical switch is triggered and completes the circuit between the power supply and the motor thus starting the rotation of the cover. Once the cover has rotated to a point where an opening in the cover is aligned with the opening of the receptacle, the user replaces the tooth brush within the receptacle, trips the mechanical switch, and opens the circuit between the power supply and the motor thus stopping the rotation of the cover.

The electronic components of the tooth brush holder may be powered by a battery or by attachment to conventional household electricity sources such as an electrical outlet. If the tooth brush holder is battery powered, the battery is preferably located within the base plate and accessed through the back of the base plate. If the tooth brush holder is powered by connection to conventional household electricity sources, the voltage typically will need to be reduced by a transformer. In the preferred embodiment, the transformer is located immediately adjacent to the prongs that allow the transformer to be pugged in to a household electrical outlet. The tooth brush holder may be electrically connected to the transformer by a conventional electric cord leading to a circuit board, power bus or other known means of distributing power to one or more electronic components within the base plate. In the preferred embodiment, the transformer may be removably secured within a cavity in the base plate with the prongs allowing connection to a household electrical outlet protruding from the surface of the base plate opposite to the rotating cover. In such a configuration, the prongs may also serve as the means for attaching the tooth brush holder to a wall. Alternatively, the transformer may be removed from the cavity and the tooth brush holder may be placed at a location remote from an electrical outlet. Under such circumstances, the transformer may be connected to the tooth brush holder by a conventional electric cord.

The tooth brush holder may be provided with one or more master power switches to shut off power to the tooth brush holder. Turning off the power by the master switch will allow a tooth brush to be removed without causing the cover to rotate. Such a feature may be useful if a user wishes to change the battery of the tooth brush holder. If desired, a switch may be included on the rear of the base plate that detects whether or not the tooth brush holder is attached to a wall. If the tooth brush holder is removed from the wall, the power to the tooth brush holder may be shut off without requiring any further action by the user.

The tooth brush holder may be used with an electric tooth brush including rechargeable models or models powered by disposable batteries. In the case of either type of electric tooth brush, the tooth brush does not need to be modified or supplemented with metallic or other material to work with a tooth brush holder that uses an electromagnetic detecting mechanism because such tooth brushes typically incorporate large amounts of electromagnetically active material such as batteries.

If the tooth brush holder is to be used with a rechargeable electric tooth brush, the charging unit of the tooth brush may be incorporated into the tooth brush holder so that the tooth brush charges when it is placed in the tooth brush holder receptacle. An alternate detecting device that may be used in the case of an electric tooth brush is to locate the power charging mechanism in the base of the receptacle and determine whether the charging mechanism is charging the tooth brush. Thus, for example but without limitation, the detecting mechanism may detect when the tooth brush is removed and the charging mechanism is no longer charging, and send a signal to the control unit indicating that the tooth brush has been removed.

In addition to the above, use of an electric tooth brush may require modification of the receptacle. The overall shape of the receptacle may be modified to accommodate the typically larger cross section of an electric tooth brush. In addition, the bottom portion of the receptacle may be modified so that the base of the electric tooth brush is supported above the base of the receptacle to ensure proper drainage and to minimize the accumulation of tooth paste residue on the bottom of the electric tooth brush. Such modification will also reduce the chance of water and tooth paste residue interfering with the charging mechanism in the case of a rechargeable tooth brush.

Further aspects of the present invention will become apparent in the following detailed description when considered in conjunction with the accompanying drawings. It should be understood, however, that the detailed description and the specific examples, while representing the preferred embodiment, are given by way of illustration only.

BRIEF DESCRIPTION OF DRAWINGS

FIG. 1 is perspective view of the improved tooth brush holder which is the subject of this invention.

FIG. 2 is a cut away front view taken along line 2—2 of FIG. 1 illustrating the interior of the rotating cover and the receptacle.

DETAILED DESCRIPTION OF PREFERRED EMBODIMENTS

Figure 4:
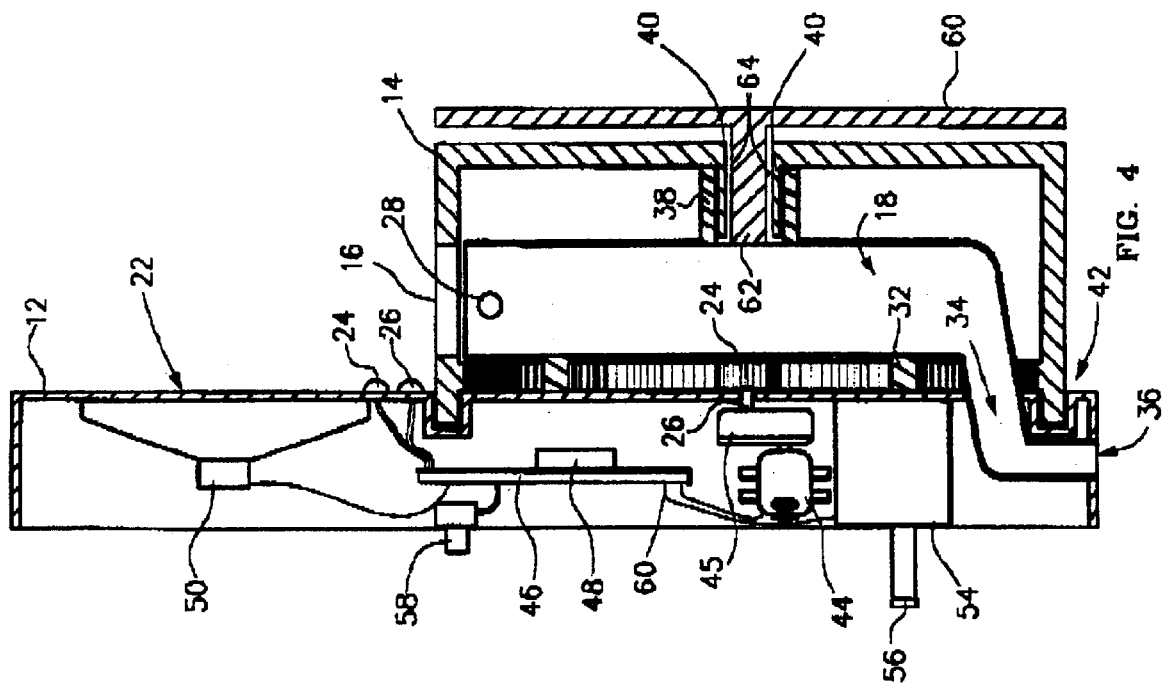
FIG. 4 is a cut away cross sectional view taken along line 4—4 of FIG. 1 illustrating the interior of the improved tooth brush holder and showing an overlay component positioned in front of the cover.

The following description is made for the purpose of illustrating the general principles of the invention and should not be taken in a limiting sense. The preferred embodiments of the invention are disclosed throughout the present application and its incorporations.

In accordance with the present invention, FIG. 1 shows an improved tooth brush holder generally designated as 10, having a base plate 12, a rotating cover 14, an opening 16 in the rotating cover, and a receptacle 18 for receiving a tooth brush. FIG. 1 also shows protruding element 19 of a mechanical switch based detecting mechanism. Protruding element 19 blocks opening 16 of cover 14 and receptacle 18 so that a tooth brush (not shown) may not be inserted into the receptacle without moving protruding element 19.

The dimensions of the receptacle 18 are such that most commonly available tooth brushes will fit whether they are long and slim or shorter and wider. Opening 16 in cover 14 is shown aligned with the opening of receptacle 18. FIG. 1 also shows master power switch 20, speaker grill 22, and light emitting diodes 24 and 26. Light emitting diode 24 may indicate that power is on. Light emitting diode 26 may be illuminated when the total accumulated run time, thus total brushing time, has reached the point when the tooth brush should be replaced.

FIG. 2 shows a cut away cross sectional view of the interior of rotating cover 14 and receptacle 18. Entrance 21 to drain canal 34 (shown in FIGS. 3 and 4) is provided in the bottom of receptacle 18. Rotating cover 14 is provided with cover gear teeth 22 which engage drive gear 24 attached to drive shaft 26.

FIG. 2 shows three different possible detecting mechanisms. Any one detecting mechanism may be used alone or two or three such detecting mechanisms may be used in combination. Receptacle 18 is provided with energy-based detecting mechanism 28 that detects the presence or absence of a tooth brush or other material. Alternatively, or in addition, receptacle 18 may be provided with electromagnetic-based detecting mechanism 30 located immediately behind receptacle 18 within base plate 12. Alternatively, or in addition, tooth brush holder 10 may be provided with a mechanical switch detecting mechanism, protruding element 19 of which is shown in FIG. 2.

Figure 3:
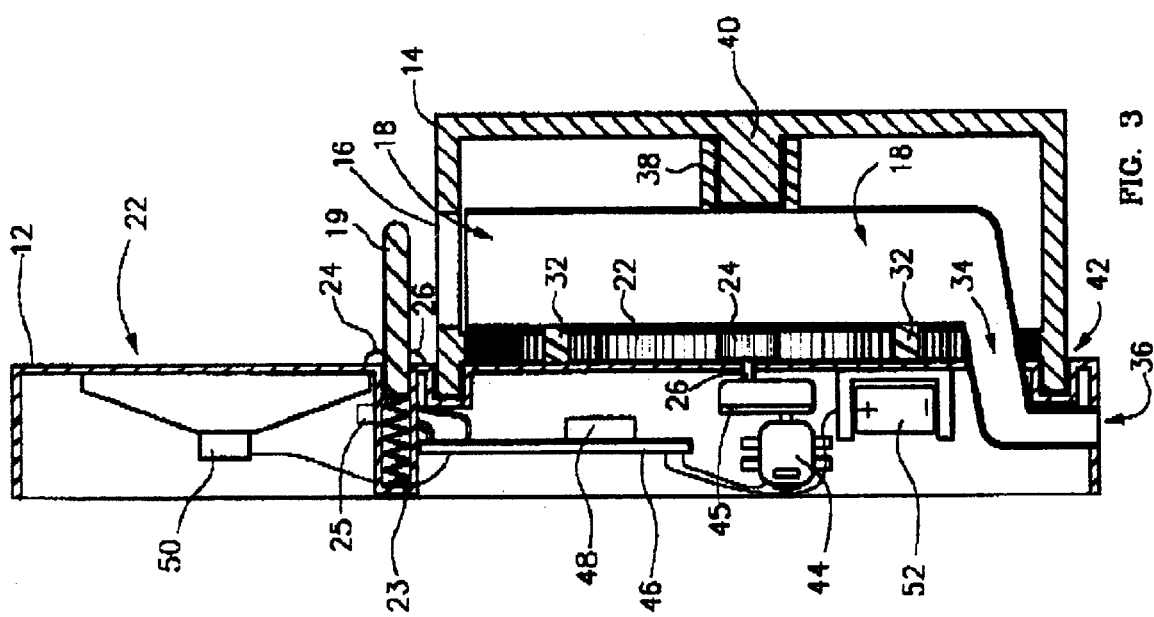
FIG. 3 is a cut away cross sectional view taken along line 3—3 of FIG. 1 illustrating the interior of the improved tooth brush holder.

FIG. 3 shows a cut away cross sectional view of the interior of base plate 12, rotating cover 14 and receptacle 18. Receptacle 18 is structurally attached to base plate 12 by supports 32 and by drain canal 34. Drain canal 34 connects receptacle 18 to drain hole 36. Receptacle 18, drain canal 34 and drain hole 36 are structured to (1) support a tooth brush (not shown); (2) allow drainage of any water and residue that may drain from the tooth brush without requiring an additional opening in rotating cover 14 to allow such drainage; (3) isolate such water and residue within receptacle 18 and drain canal 34 and away from the mechanical, electronic, and other components of the tooth brush holder; and (4) minimize the chance of any blockage of drain canal 34 by accumulated residue or any other foreign matter. It is preferred to structure receptacle 18 as small as possible to reduce the total bulk of tooth brush holder 10, however, receptacle 18 also should be structured to accommodate as may different shapes of tooth brushes as possible.

Bearing socket 38 is attached to receptacle 18 and contains axle 40 of rotating cover 14. The annular lip of rotating cover 14 fits into annular groove 42 in base plate 12. The interior annular surface of rotating cover 14 is provided with cover gear teeth 22 which are engaged by drive gear 24 attached to drive shaft 26 connecting gear box 45.

Motor 44 is located within base plate 12 and is connected to gear box 45 such that activation of motor 44 results in rotation of rotating cover 14. Motor 44 is controlled by a control mechanism 48 mounted on circuit board 46. The presence or absence of a tooth brush (not shown) within receptacle 18 is detected by a detecting mechanism. The detecting mechanism shown in FIG. 3 consists of protruding element 19, spring 23, and sensing means 25. Spring 23 biases protruding element 19 in an outward direction perpendicular to the face of base plate 12. When a user wishes to insert a tooth brush (not shown) into receptacle 18, the user pushes against protruding element 19 and moves protruding element 19 at least partially back into base plate 12. As shown, the edge of protruding element 19 may be rounded so that a generally downward force is translated into a generally horizontal force that moves protruding element 19 at least partially back into base plate 12. Sensing means 25 may determine whether protruding element 19 is fully extended (as shown) indicating the absence of a tooth brush (not shown) in receptacle 18 or whether the protruding element 19 is positioned partially back within base plate 12 (not shown) indicating the presence of a tooth brush (not shown). Sensing means 25 may be a micro switch. Alternatively, sensing means 25 may detect movement of protruding element 19, and if desired, the direction of such movement. Such movement will indicate a change of state with respect to the presence or absence of a tooth brush (not shown) within receptacle 18. If the direction of such movement also is detected, that direction will indicate whether the change of state corresponds to an insertion of a tooth brush or the removal of a tooth brush.

Control mechanism 48 also is connected to and controls light emitting diodes 24 and 26 and the components (not shown) that store, decode, and amplify any optional audio program. Such audio program components also may be mounted on circuit board 46. The audio program may be played through speaker 50 located inside base plate 12 behind speaker grill 22. In FIG. 3, the improved tooth brush holder is shown powered by battery 52.

FIG. 4 shows the improved tooth brush holder adapted to be powered by conventional household power such as an electrical socket (not shown). Prongs 56 are adapted to be inserted into a household electrical socket and are attached to transformer 54. Prongs 56 not only supply power to the improved tooth brush holder but also allow the tooth brush holder to be mounted to a wall (not shown) by plugging prongs 56 into an electrical outlet (not shown). Transformer 54 is removably secured within a cavity in base plate 12. Alternatively, transformer 54 may be removed from base plate 12 allowing the improved tooth brush holder to be located away from an electrical socket. Power cord 60 connects the improved tooth brush holder to transformer 54. Switch 58 is located on and protrudes from the rear surface of base plate 12. When the improved tooth brush holder is attached to a wall (not shown), switch 58 is depressed, allowing the improved tooth brush holder to function. When the improved tooth brush holder is removed from a wall, switch 58 is no longer depressed, turning off the power to the improved tooth brush holder.

FIG. 4 also shows overlay 60 positioned in front of rotating cover 14. Overlay 60 is attached to receptacle 18 by support 62. In the embodiment pictured in FIG. 4, axle 40 is a ring structure that fits inside bearing socket 38 which, in turn, is attached to receptacle 18. The ring structure of axle 40 allows support 62 to connect overlay 60 with receptacle 18. Overlay 40, as shown in FIG. 4, does not rotate. To provide an overlay that rotates in the opposite direction from the rotating cover, a gear (not shown) may be positioned in gap 64, corresponding gear teeth may be provided on support 62 and the interior annular surface of axle 40, and support 62 may be provided with a bearing surface that holds support 62 in place and allows support 62 to rotate.

In operation, when a tooth brush is removed from receptacle 18, its removal is detected by detecting mechanism 28 detecting mechanism 30 the mechanical switch detecting mechanism shown in FIGS. 1, 2, and 3, or any other detecting mechanism described in this application. The detecting mechanism sends a signal to control unit 48. Control unit 48 causes motor 44 to turn. Gear box 45 causes drive shaft 26 to turn at a slower speed and with more force than the initial rotation provided by motor 44. Drive shaft 26 turns drive gear 24 which causes rotating cover 14 to begin rotation. Control unit 48 may also start an audio program that is played through speaker 50. Once rotating cover 14 begins rotation, opening 16 passes out of alignment with the opening of receptacle 18 thus preventing the tooth brush from being replaced until one complete rotation has been completed. Once rotating cover 14 has completed a full rotation and opening 16 is once again aligned with the opening of receptacle 18, control unit 48 stops the rotation of rotating cover 14 allowing the tooth brush to be replaced in receptacle 18.

Although the invention has now been described in terms of certain preferred embodiments and exemplified with respect thereto, one skilled in art can readily appreciate that various modifications, changes, omissions and substitutions may be made without departing from the spirit thereof It is intended therefore that the present invention be limited solely by the scope of the following claims.

What is claimed is:

1. A tooth brush holder comprising:

a base plate;

a rotatable cover defining at least one opening;

a receptacle positioned substantially outside said base plate and adapted to receive a portion of a tooth brush;

said cover adapted to allow access to said receptacle when said cover is in one position and block access to said receptacle when said cover is in a second position;
a driving mechanism for changing the position of said cover; and
a detecting mechanism.

2. The tooth brush holder of claim 1 wherein the detecting mechanism comprises a mechanical switch adapted so that the switch is in one state when a tooth brush is present within the receptacle and is in a different state when the tooth brush is absent from the receptacle.

3. The tooth brush holder of claim 1 wherein the mechanical switch is located outside the receptacle and proximate to the cover opening.

4. The tooth brush holder of claim 1 wherein the detecting mechanism comprises an energy-based emitter and receiver.

5. The tooth brush holder of claim 1 wherein the detecting mechanism comprises an electromagnetic sensor.

6. The tooth brush holder of claim 4 wherein the electromagnetic sensor detects electromagnetically active material associated with a tooth brush.

7. A tooth brush holder comprising:
a base plate; a rotatable cover defining at least one opening;
a receptacle positioned substantially outside said base plate and adapted to receive a portion of a tooth brush;
said receptacle having a drain adapted to pass through said base plate;
said cover adapted to allow access to said receptacle when said cover is in one position and block access to said receptacle when said cover is in a second position;
a driving mechanism for changing the position of said cover;
a detecting mechanism; and
a control mechanism responsive to said detecting mechanism for controlling the position of the cover.

8. A tooth brush holder as defined by claims 1, 2, 3, 4 or 5 further comprising a control mechanism for controlling the position of said cover, and said control mechanism being responsive to said detecting mechanism.

9. The tooth brush holder of claims 1, 2, 3, 4 or 5 wherein the driving mechanism comprises a motor.

10. The tooth brush holder of claims 1, 2, 3, 4 or 5 wherein said driving mechanism comprises a motor mounted within the base plate.

11. The tooth brush holder of claims 1, 2, 3, 4 or 5 wherein said driving mechanism comprises a motor mounted within the base plate and a gear box for slowing the rotation speed of the driving mechanism.

12. The tooth brush holder of claims 1, 2, 3, 4 or 5 wherein said driving mechanism comprises a motor mounted within the base plate and reducing means for slowing the rotation speed of the driving mechanism.

13. The tooth brush holder of claims 1, 2, 3, 4 or 5 wherein said receptacle has a drain; and said receptacle drain is adapted pass through said base plate.

14. The tooth brush holder of claim 13 further comprising an overlay attached to said rotatable cover.

15. The tooth brush holder of claim 14 wherein the cover overlay rotates when said rotatable cover rotates.

16. The tooth brush holder of claim 13 further comprising an overlay positioned proximate to said rotatable cover.

17. The tooth brush holder of claim 14 wherein the cover overlay remains stationary when said rotatable cover rotates.

18. The tooth brush holder of claim 7 wherein said cover overlay defines at least one opening allowing the surface of said rotating cover to be viewed through said opening.

19. The tooth brush holder of claim 7 wherein the driving mechanism comprises a motor.

20. The tooth brush holder of claim 7 wherein said driving mechanism comprises a motor mounted within the base plate.

21. The tooth brush holder of claim 7 wherein said driving mechanism comprises a motor mounted within the base plate and a gear box for slowing the rotation speed of the driving mechanism.

22. The tooth brush holder of claim 7 wherein said driving mechanism comprises a motor mounted within the base plate and reducing means for slowing the rotation speed of the driving mechanism.

23. The tooth brush holder of claim 22 further comprising cover overlay means for changing the appearance of said tooth brush holder.

24. A tooth brush holder comprising:
base plate;
a rotatable cover defining at least one opening;
a receptacle positioned substantially outside said base plate and adapted to receive a portion of a tooth brush;
said receptacle having a drain adapted to pass through said base plate;
said cover adapted to allow access to said receptacle when said cover is in one position and block access to said receptacle when said cover is in a second position;
means for changing the position of said cover;
means for detecting the presence or absence of a tooth brush within the receptacle; and
said means for changing the position of said cover being responsive to said detecting means.

25. The tooth brush holder of claim 21 further comprising control means responsive to said detecting means for controlling the position of the cover.

26. The tooth brush holder of claim 21 further comprising cover overlay means for changing the appearance of said tooth brush holder.

27. The tooth brush holder of claims 25 or 26 wherein said cover overlay means is attached to said rotating cover.

28. The tooth brush holder of claims 25 or 26 wherein said cover overlay means is proximate said rotating cover and rotates when said cover rotates.

29. The tooth brush holder of claims 25 or 26 wherein said cover overlay means is proximate to said rotating cover and remains stationary when said rotating cover rotates.

30. The tooth brush holder of claims 25 or 26 wherein said cover overlay means defines at least one opening allowing the surface of said rotating cover to be viewed through said opening.

31. The tooth brush holder of claims 1, 2, 3, 4, 5, 7, 24, 25, or 26 further comprising means for producing one or more audio programs.

32. The tooth brush holder of claims 1, 2, 3, 4, 5, 7, 24, 25, or 26 further comprising a radio.

33. The tooth brush holder of claims 1, 2, 3, 4, 5, 7, 24, 25 or 26 further comprising means for indicating when it is time to replace the tooth brush.

34. The tooth brush holder of claims 24, 25, or 26 wherein said means for changing the position of said cover comprises a motor mounted within the base plate.

35. The tooth brush holder of claims 24, 25, or 26 wherein said means for changing the position of said cover comprises a motor mounted within the base plate and a gear box for slowing the rotation speed of the motor.

36. The tooth brush holder of claims 24, 25, or 26 wherein said means for changing the position of said cover comprises a motor mounted within the base plate and reducing means for slowing the rotation speed of the motor.

37. The tooth brush bolder of claims 1, 2, 3, 4, 5, 7, 24, 25, or 26 further comprising means for electrically connecting said tooth brush holder to a household electrical outlet; and said means for electrically connecting adapted to be removably secured to said base plate.

38. The tooth brush holder of claims 1, 2, 3, 4, 5, 7, 24, 25, or 26 further comprising:

prongs adapted to fit into a household electrical outlet;

a transformer to reduce conventional household voltage to a voltage usable by the tooth brush holder;

means for electrically connecting said transformer to said tooth brush holder; and wherein said base plate and said transformer are adapted so that said transformer may be removably secured to said base plate.

39. The tooth brush holder of claims 1, 2, 3, 4, 5, 7, 24, 25, or 26 wherein the receptacle is adapted to receive an electric tooth brush.

40. The tooth brush holder of claims 1, 2, 3, 4, 5, 7, 24, 25, or 26 wherein the receptacle is adapted to receive an electric tooth brush and is further adapted to function as a charging unit for a rechargeable electric tooth brush.

41. The tooth brush holder of claim 7, wherein:

the receptacle is adapted to receive an electric tooth brush;

the receptacle is further adapted to function as a charging unit for a rechargeable electric tooth brush; and the detecting mechanism comprises a mechanism for determining whether the charging unit is charging the tooth brush.

* * * * *